United States Patent [19]

Sargeson et al.

[11] Patent Number: 4,497,737
[45] Date of Patent: Feb. 5, 1985

[54] METAL CAGE COMPLEXES AND PRODUCTION THEREOF

[75] Inventors: Alan M. Sargeson; Anthony J. Herlt, both of Curtin; John M. Harrowfield, Kardinya, all of Australia

[73] Assignee: The Australian National University, Australia

[21] Appl. No.: 355,663

[22] Filed: Mar. 8, 1982

Related U.S. Application Data

[63] Continuation of Ser. No. 954,314, Oct. 24, 1978, abandoned.

[30] Foreign Application Priority Data

Oct. 26, 1977 [AU] Australia .............................. PD2201
Oct. 26, 1977 [AU] Australia .............................. PD2202

[51] Int. Cl.$^3$ ............................................ C07D 487/08
[52] U.S. Cl. ......................... 260/239 BC; 260/429 J; 260/429 R; 260/439 R; 260/438.5 R; 260/438.1
[58] Field of Search ................................. 260/239 BC

[56] References Cited

PUBLICATIONS

Green et al, Inorg. Chem., vol. 2, No. 3, Jun. 1963, pp. 597–660.
Creaser et al, J.A.C.S., 99, pp. 3181 & 3182, (1977).

Primary Examiner—Glennon H. Hollrah
Assistant Examiner—D. B. Springer
Attorney, Agent, or Firm—Bacon & Thomas

[57] ABSTRACT

Hydrogen peroxide is produced by oxidation of a coordination complex of a metal ion capable of existing in at least two oxidation states and a ligand, the coordination complex being sufficiently stable for the metal ion to be oxidized and reduced without decomposition of the complex and the metal ion being in its lower oxidation state. In a cyclic process, the step of reduction of the complex with the metal ion in its higher oxidation state precedes the oxidation step, and the reduction and oxidation steps are repeated sequentially. Novel coordination complexes which may be used in the process have the formula:

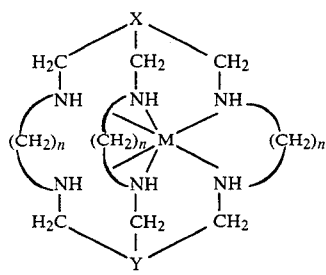

in which n represents an integer; M represents a cobalt ion or other metal ion having at least two oxidation states; x and y, which may be the same or different, each represent $\equiv$N, $\equiv$P or $\equiv$C—R', in which R' represents a hydrogen or halogen atom, or a hydroxyl, nitro, nitroso, amino, alkyl, or cyano group, or a group of the formula —COOR", —COCOOR" or —NH—CO—CH—CHCOOR" in which R" is a hydrogen atom or alkyl group; provided that when M represents a cobalt ion and n is 2, x and y do not both represent $\equiv$N.

4 Claims, No Drawings

METAL CAGE COMPLEXES AND PRODUCTION THEREOF

This application is a continuation of application Ser. No. 954,314, filed 10/24/78, abandoned.

This invention relates to the production of hydrogen peroxide using metal complexes, and to novel metal complexes and to the preparations thereof. In one particular aspect, the invention relates to metal complexes in which the ligands are linked to form a cage-like structure for the metal ion.

Hydrogen peroxide may be produced by means of a technique according to which one or more anthraquinones are catalytically hydrogenated to form anthraquinols and the anthraquinols are then oxidised to regenerate anthraquinone and synthesise hydrogen peroxide. The technique has been embodied in large scale commercial processes in which a hydrophobic organic solvent system carries the anthraquinol or anthraquinone compounds in solution and the hydrogen peroxide is recovered from the solvent system by aqueous extraction.

The present invention provides a technique for the production of hydrogen peroxide which also involves a series of reactions culminating in the regeneration of the starting material and which may therefore be considered to be an alternative form of cyclic process to that described above.

According to the present invention, there is provided a process for the production of hydrogen peroxide comprising the steps of:

(i) oxidising a coordination complex of a metal ion capable of existing in at least two oxidation states and a ligand, said coordination complex being sufficiently stable for the metal ion to be oxidised and reduced without decomposition of the complex and said metal ion being in its lower oxidation state; and (iii) recovering hydrogen peroxide produced thereby.

Preferably, the process is a cyclic process wherein the step of reduction of said coordination complex with the metal ion in its higher oxidation state precedes the oxidation step described above, and the reduction and oxidation steps are repeated sequentially.

In its general concept then, the present invention provides a technique for the production of hydrogen peroxide which involves the use of a metal ion in the form of a coordination complex with a ligand, which coordination complex is sufficiently stable for the metal to be reduced and re-oxidised without complete destruction of the complex. The complex is preferably stable enough to inhibit ligand substitution under the conditions employed, at least to a great extent, as undue decomposition of the metal complex in use could render a cyclic commerical process utilising the complex unecomomic.

In one embodiment of the invention, oxidation of the complex may be performed by passing oxygen-saturated water through the complex supported on a suitable support, the oxygen in the water being reduced to hydrogen peroxide concomitantly with the oxidation of the complex. The concentration of hydrogen peroxide in the water may be increased by several passages through the complex-support system and the hydrogen peroxide so produced may be recovered by any suitable means, for example by distillation.

The hydrogen peroxide produced by means of at least the preferred or particularly envisaged embodiments of the present invention is relatively stable as the metal ion is trapped in the complex to such a great extent that it is less available, for practical purposes, to act as a decomposition catalyst.

This invention therefore also provides hydrogen peroxide whenever produced by the process of this invention.

Relatively stable complexes envisaged for use in the practice of this invention may be formed from complexes in which a number of separate ligands are complexed, e.g. chelated, to a central metal ion by chemically linking the separate ligands to form a cage-like structure. The linking or "capping" groups may be, for example, tris-(methylene) amino or tris-(methylene) methane moieties. The particular linking mechanism used and the method of achieving the necessary chemical reactions may be suitably selected and performed in the light of the desired effect and the general priniciples of chemistry. The separate ligands so linked or "capped" may be suitably selected from known ligands and may for example, be suitably selected from di- or polyamines or other nitrogen based ligands. The number of effective coordinating groups in such ligands is preferably not more than half and particularly preferably not more than a third of the coordination number of the metal ion in its oxidised state in the process envisaged. Suitably linked or "capped" tris-(ethylenediamine) or 1,9-diamino-5-(methyl)-5-(4-amino-2-azabutyl)-3,7-diazanonane ligands are particularly envisaged.

Metal ions which may be used according to this invention may be selected from those having two or more oxidation states which form stable coordination complexes in at least two of those states. An example of such a metal is cobalt, stable complexes of which can exist in the (111) or the (11) oxidation states. Rhodium, chromium or platinum also provide useful metal ions for use according to this invention although other metals may be suitably selected from the general principles set out above.

Particularly envisaged in one aspect of the invention for use in the production of hydrogen peroxide by the technique of this invention is the complex (S) [1,3,6,8,10,13,16,19-octaazabicyclo [6.6.6.] eicosane) cobalt (111)]$^{3+}$. This complex has been given the trivial name [Co(sepulchrate)]$^{3+}$ in keeping with the cryptate nomenclature ('sepulchrate' may hereafter be abbreviated to 'sep'), and may be prepared by condensing tris(ethylenediamine)cobalt (111) with 2 molecules of ammonia and 6 molecules of formaldehyde to form a cage-like structure. (Further details of the structure and preparation of this complex are given in I. I. Creaser, J. MacB. Harrowfield, A. J. Herlt, A. M. Sargeson, J. Springborg, R. J. Geue and M. R. Snow, J. Amer. Chem. Soc., 99, 3181 (1977).

In a further aspect, this invention provides novel coordination complexes which may be used in the process of the present invention, the novel complexes having the general formula

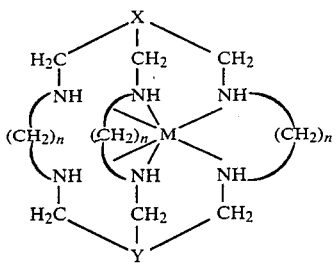

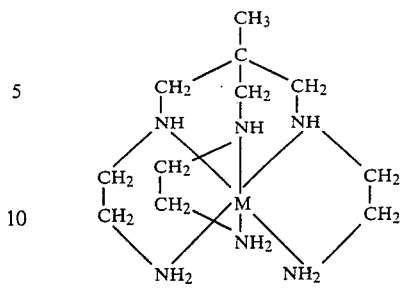

in which n represents an integer, preferably from 2 to 4; M represents a cobalt ion or other metal ion having at least two oxidation states, preferably Co, Rh, Pt, Cr, Cu, Re, Mo, W, Ni, V or Fe; and X and Y, which may be the same or different, each represent ≡N, ≡P or ≡C—R', in which R' represents a hydrogen or halogen (preferably chlorine or bromine) atom, or a hydroxyl, nitro, nitroso, amino, alkyl (preferably $C_1$–$C_6$), or cyano group, or a group of the formula —COOR'', —COCOOR'' or —NH—COCH=CHCOOR'' in which R'' is a hydrogen atom or alkyl (preferably $C_1$–$C_6$) group; provided that when M represents a cobalt ion and n is 2, x and y do not both represent ≡N.

The novel coordination complexes of this aspect of the invention may be prepared by the condensation of a tris-(diamine)metal ion complex of the formula:

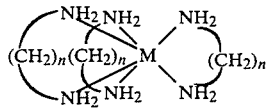

in which M and n are as described above, with formaldehyde and an appropriate nucleophile (preferably selected from $NH_3$, $P(CH_2OH)_4^+$, and $CH_3$—R', in which R' is as described above).

Whilst the present invention is not intended to be in any way limited by any postulated mechanism, it is believed that this synthesis arises from the condensation of formaldehyde at a coordinated amine of the tris-(diamine) metal ion complex to give an activated imine to which the nucleophile adds.

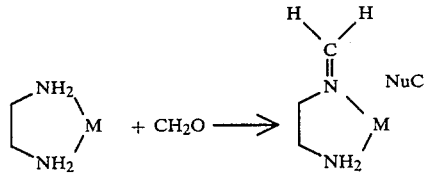

Subsequent additions of the carbonyl reagent at the diamine centres and intramolecular attack by the nucleophile now attached to the complex leads to the first "cap". The same process repeated on the other trigonal face of the complex produces the "cage-like structure" of the complex of this invention.

In an alternative synthesis, certain of the novel complexes of this aspect of the invention may be prepared by condensation of a metal chelate of 1,9-diamino-5-(methyl)-5-(4-amino-2-azabutyl)-3,7-diazanonane of the formula:

in which M is as described above, with formaldehyde and a nucleophile as described above.

In addition, functional groups represented by R' in the complexes of the present invention may be substituted by other functional groups falling within the definition by methods known in the art. By way of example, when R' represents a chloro group, treatment of the complex with Zn dust and HCl will give a complex in which R' represents a hydrogen atom. Similarly, where R' represents an amino group, treatment of the complex with $NO^+$ in the presence of $Cl^-$ will give a complex in which R' represents a hydroxyl, a chloro or a nitro group.

Some of the novel complexes of this aspect of the invention have been found to have extraordinary stability and they therefore have general uses as inert oxidation-reduction regents in both inorganic and organic oxidation and reduction reactions, both for synthesis and as mechanistic probes, in addition to the quantitative reduction of $O_2$ to $H_2O_2$.

Another important property of the cage-like structure of these novel complexes is that the metal does not escape the cage without rupture of the cage. The possibility thus exists that the redox potential will be altered radically in the electronically excited states and under these circumstances the complexes might be especially reactive in excited states and the possibility for reduction of water to hydrogen exists or the oxidation to $O_2$ with suitable choices of redox couples and wave-length of the incident radiation.

The cage-like structures also offer unique possibilities for the production of ion exchange resins where the cage is tied to the polymer support through a suitable substituent on the cap, such as an $NH_2$-group. One of the special advantages of such ion exchange resins would be to construct them with the chiral cages, so that the resin has the charge and asymmetric sites coincident. Such resins could be used for resolving racemic organic anions, for example amino acids. Another interesting possibility is the use of the metal ion cages attached to a resin surface as an electrode surface. Electron transfer between the Co(II)/Co(III) cages is extraordinarily fast ($10^5$-fold) compared to the parent ethylenediamine complexes. Side-by-side on a surface, the exchange should be even more rapid.

In summary, the complexes of this invention have utility as stable redox reagents for inorganic and organic synthesis where the metal is no longer available for coordination to the reacting substrates and the redox reagents can be considered as a source or sink for electrons. This redox behaviour can be extended to photochemical redox reactions with a variety of metals, where one is no longer dependent on the property of the metal to keep the complexes intact, with the same constitution, over the course of the reaction. Finally, their charge and chiral properties make them interesting reagents to fix to resins for ion exchange desalination, supported redox reagents and supported resolving agents to separate enantiomers.

The following table of redox potentials demonstrates the effect of the cage-substituents on the metal in the novel complexes of the present invention.

| Redox Potentials Voltammograms in 0.1 NaClO$_4$/SCE | | |
|---|---|---|
| Complex | AC Voltammetry E V | Cyclic Voltammetry Δ E mV |
| [Co(sar)]Cl$_3$ | −0.41 | 90$^a$ |
| [Co(azamesar)]Cl$_3$ | −0.60 | 70$^b$ |
| [Co(dinosar)] (CF$_3$SO$_3$)$_3$ | −0.23 | 70$^b$ |
| [Co(ammesar)] Cl$_3$.HCl | −0.64 | |
| [Co(diamsar)] Cl$_3$.2HCl | −0.275 | 75$^a$ |
| [Pt(sep)]Cl$_4$ | −0.31 | 180$^b$ |

$^a$200 mV/sec
$^b$100 mV/sec

Preferred novel complexes of this aspect of the invention, together with details of their preparation and the trivial names given to them, and further details of the production of hydrogen peroxide in accordance with the present invention are given in the following examples which are included by way of exemplification of the invention.

EXAMPLE 1

Preparation of [Co(Sepulchrate)]Cl$_3$

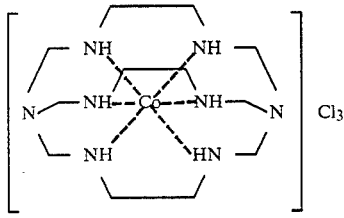

To a stirred solution of Li$_2$CO$_3$ (50 g) in a solution of (±)-[Co(en)$_3$]Cl$_3$ (9.1 g, 0.025 mol) in water (125 ml) was added aqueous ammonia (166 ml, 2.5 mol) diluted to 592 ml and aqueous formaldehyde (952 ml, 7.5 mol). The solutions were added separately and dropwise over 2 h using a peristaltic pump. The mixture was stirred for another half hour, the Li$_2$CO$_3$ filtered off and the pH of the filtrate adjusted to ~3 with 12M HCl. The solution was diluted to ~8 liters and sorbed on an ion exchange column (Dowex 50-WX2, 200-400 mesh, H$^+$ form, 5×10 cm). The column was eluted with Na$_3$citrate (5 liters of 0.2M) to remove a pink species which was discarded. The resin bed was then washed with H$_2$O and 1M HCl to remove Na$^+$ and the orange species removed from the column by eluting with HCl (3M, ~3 liters). The eluate was taken down to dryness on a vacuum evaporator at 50° C. The isolated compound was recrystallised by dissolving it in water (~90° C.) and adding acetone dropwise, while cooling in an ice bath and stirring.

Yield 16.7 g, 74%.

Analysis: Calcd for CoC$_{12}$N$_8$H$_{30}$Cl$_3$: Co, 13.05; C, 31.91; N, 24.81; H, 6.69; Cl, 23.54. Found: Co, 12.85; C, 31.30; N, 25.55; H, 7.16; Cl, 22.79.

The optically active forms (R)-[Co(sep)]Cl$_3$.H$_2$O and (S)-[Co(sep)]Cl$_3$.H$_2$O were prepared similarly starting with Δ-[Coen$_3$]Cl$_3$ and Λ-[Coen$_3$]Cl$_3$ respectively. [Co(sep)]$^{3+}$ was reduced to [Co(sep)]$^{2+}$ with Zn dust in H$_2$O under N$_2$ and isolated as [Co(sep)]ZnCl$_4$.H$_2$O.

Analysis Calcd. for CoC$_{12}$N$_8$H$_{30}$ZnCl$_4$.H$_2$O: Co, 10.33; C, 25.25; N, 19.64; H, 5.65; Cl, 24.85. Found: Co, 10.50; C, 25.59; N, 19.15; H, 5.75; Cl, 25.36.

H$_2$O$_2$ Production

The stoichiometry of the production of H$_2$O$_2$ in accordance with this invention is given by:

$$2Cosep^{2+} + O_2 + 2H^+ \rightarrow 2Cosep^{3+} + H_2O_2 \quad (1)$$

The Cosep$^{3+}$ may be identified by its visible spectrum and H$_2$O$_2$ by its reaction with iodide to free iodine.

An aqueous solution of Cosep$^{2+}$ made in situ by reduction of Cosep$^{3+}$ with Zn dust or amalgamated Zn was mixed with a large volume of oxygen-saturated water containing O$_2$ in 2.5 to 14 fold excess. After ~½ hr the solutions were acidified with a small volume of conc. HCl to dissolve the precipitate of Zn hydroxide. The Cosep$^{3+}$ was then determined spectrophotometrically at 472 nm where the cation Cosep$^{3+}$ has its first ligand field band ($\epsilon$=109). The concentration of H$_2$O$_2$ was determined iodometrically. The concentrations of O$_2$ in the oxygen-saturated water were obtained from table values. The results are summarised below:

| [Cosep$_M^{2+}$] × 10$^4$ | [H$_2$O$_2$] × 10$^4$ | % of theoretical concentration |
|---|---|---|
| 1.74 | 0.91 | 105 |
| 2.33 | 1.11 | 95 |
| 4.57 | 2.25 | 98 |
| 7.30 | 3.52 | 96 |

All oxidations were done in H$_2$O at pH~7, and with [O$_2$]=1.3×10$^{-3}$M. The theoretical concentrations of H$_2$O$_2$ were calculated according to equation (1).

EXAMPLE 2

Preparation of [Co(dinosar)]Cl$_3$.H$_2$O

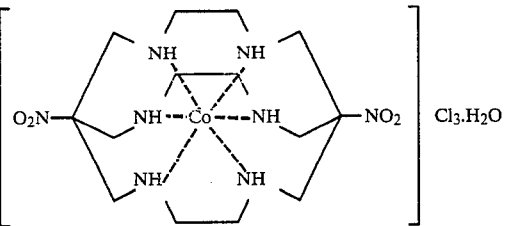

Na$_2$CO$_3$ (21.5 g) was added to a solution of [Co(en)$_3$]Br$_3$ (51.5 g), CH$_3$NO$_2$ (64 g) and HCHO solution (37%, 430 g) in H$_2$O (2 liters). After 4 h the reaction was quenched by the addition of CH$_3$CO$_2$H until the pH fell below 5. After the CO$_2$ effervescence had died down, HClO$_4$ (70%, 100 ml) was added, causing immediate precipitation of a yellow-orange solid. After cooling for 90 min in an ice bath, the solid was collected, washed with ice-cold dilute HClO$_4$, ethanol and air dried. Yield: 64 g. The isolated compound was dissolved in H$_2$O, sorbed on a cation exchange column (Dowex 50-WX2, 200–400 mesh, H+ form), washed with H₂O and 1M HCl and eluted with 3M HCl. The eluate was taken down to a small volume under vacuum and crystallization of the complex was completed by the addition of ethanol and cooling in an ice bath.

Analysis: Calcd for CoC$_{14}$N$_8$H$_{30}$O$_4$Cl$_3$.H$_2$O: Co, 10.57; C, 30.15; H, 5.79; N, 20.09; Cl, 19.07. Found: Co, 10.57; C, 30.35; H, 5.61; N, 19.99; Cl, 19.10.

[Co(dinosar)]$^{3+}$ was reduced to [Co(dinosar)]$^{2+}$ with Zn dust in H₂O in a N₂ atmosphere and isolated as [Co(dinosar)](ClO$_4$)$_2$.

Analysis: Calcd for CoC$_{14}$N$_8$H$_{30}$O$_{12}$Cl$_2$: Co, 9.32; C, 26.60; H, 4.78; N, 17.72; Cl, 11.21. Found: Co, 9.52; C, 26.29; H, 4.78; N, 17.27; Cl, 11.25.

EXAMPLE 3

Preparation of [Co(diamsar)]Cl$_3$.2HCl

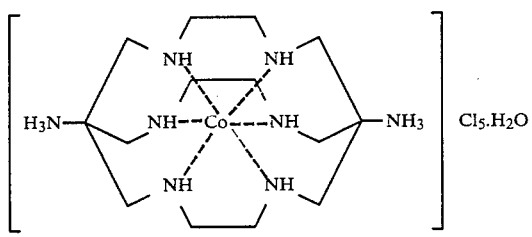

[Co(dinosar)]Cl$_3$ (40 g) was dissolved in H₂O (2 liters) and the solution deoxygenated with N₂. While maintaining the N₂ flow and stirring vigorously, Zn dust (40 g) was added. Conc. HCl (200 ml) was added dropwise, and the N₂ flow and stirring were continued for 1 h after the addition of the HCl was complete. The N₂ flow was then stopped and 30% H₂O₂ (50 ml) was added to the green solution. The resulting orange-yellow solution was warmed on the steam bath for 15 min, cooled and sorbed on a cation exchange column (Dowex 50-WX2, 200–400 mesh, H+ form) and the column was washed with H₂O (2 liters) and HCl (1M, 2 liters). The complex was then eluted with 3M HCl and the eluate reduced in volume under vacuum until crystallization commenced. Deposition was completed by the addition of ethanol, and the crystals were collected and washed with ethanol and ether.

Yield: 39 g, 94%.

Analysis: Calcd for CoC$_{14}$H$_{36}$N$_8$Cl$_5$.H$_2$O: Co, 10.33; C, 29.46; H, 6.71; N, 19.63; Cl, 31.06. Found: Co, 10.15; C, 29.57; H, 6.67; N, 19.07; Cl, 30.22.

[Co(Diamsar)]$^{3+}$ was reduced to [Co(diamsar)]$^{2+}$ with Zn and HCl and isolated as [Co(diamsar)](NO$_3$)$_2$.2HNO$_3$.

Analysis: Calcd for CoN$_{12}$C$_{14}$H$_{36}$O$_{12}$: Co, 9.45; C, 26.97; H, 5.81; N, 26.97. Found: Co, 9.56; C, 26.28; H, 5.89; N, 26.73.

H₂O₂ Production

[Co(diamsar)]$^{2+}$ may be utilised in the reduction of oxygen to produce hydrogen peroxide as described in Example 1. The rate constant (R$_{ox}$) for oxidation of [Co(diamsar)]$^{2+}$ by oxygen followed spectrophotochemically at M=0.2M (NaCl, HCl) and 25° C. is found to be 22$\mu^{-1}$S$^{-1}$.

EXAMPLE 4

Preparation of [Pt$^{IV}$(dinosar-H)]Cl$_3$.3H$_2$O

[Pt(en)$_3$]Cl$_4$ (22.52 g), CH$_3$NO$_2$ (26.57 g), HCHO (38% aqueous solution, 48.19 g) and Na$_2$CO$_3$.10H$_2$O (8.78 g) were combined in H₂O (1130 ml) and the solution was left at room temperature, in the dark, for 4 h. The resultant orange solution was acidified to pH 1 (HCl), and reduced to dryness under vacuum (bath temperature <40° C.). The solid residue was extracted with H₂O (~70 ml) and the solution was passed through a short hyflo column to yield a clear orange-brown solution. This was concentrated under vacuum to ~50 ml volume, and then repeatedly passed through short (1″) Sephadex SPC-25 (Na+ form) columns (which preferentially adsorbed a brown-black sideproduct) until a clean orange band appeared on the column. The resultant golden-orange solution was concentrated to ~50 ml under vacuum (bath temperature <40° C.) and refrigerated (4 h). The bright orange crystals were collected and washed with ethanol and ether. Yield 10.1 g. Reduction in volume of the filtrate yielded a further 4 g of the mono-deprotonated complex. The product was recrystallised from the minimum volume of hot water (80° C.).

Analysis: Calcd for PtC$_{14}$H$_{29}$N$_8$O$_4$Cl$_3$.3H$_2$O: C, 23.08; H, 4.81; N, 15.38; Cl, 14.61. Found: C, 23.54; H, 4.93; N, 15.39; Cl, 14.81.

EXAMPLE 5

Preparation of [Pt$^{IV}$(dinosar)]Cl$_4$.3H$_2$O HCl

[Pt$^{IV}$(dinosar-H)]Cl$_3$.3H$_2$O (1.0 g) was dissolved in the minimum volume of hot H₂O (80° C.), then rapidly diluted with an equal volume of conc. HCl. Colourless rods slowly separated on cooling to room temperature. The solution was refrigerated (6 h), then the product was collected and washed with ethanol and ether.

Yield: 0.7 g.

Analysis: Calcd for Pt C$_{14}$H$_{30}$N$_8$O$_4$ Cl$_4$.3H$_2$O.HCl: C, 20.96; H, 4.62; N, 13.97; Cl, 22.11; Pt, 24.33 Found: C, 21.38, H, 4.66; N, 14.05; Cl, 22.10; Pt, 24.38.

EXAMPLE 6

Preparation of [Pt$^{IV}$(sepulchrate)]Cl$_4$

To a stirred solution of Li$_2$CO$_3$ (10 g) in a solution of [Pt(en)$_3$]Cl$_4$ (4.7 g, 9×10$^{-3}$ mol) in H₂O (50 ml) was added aqueous ammonia (62 ml, 0.92 mol) diluted to 218 ml and formaldehyde (38%, 218 ml, 2.75 mol). The solutions were added separately and dropwise over 5 h by a peristaltic pump. The pH of the reaction mixture was then adjusted to ~1 with conc. HCl and sorbed on an ion exchange column (Dowex 50-WX2, H+ form). The column was washed with H₂O and 1M HCl and the Pt$^{IV}$ species were removed with 6M HCl. The eluate was taken down to dryness on a vacuum evaporator, and the residue dissolved in water, filtered and sorbed on a Sephadex SPC-25 ion exchange column. On elution with 0.1M Na$_2$ tartrate, two bands separated. The eluate containing the first and largest band was poured on to a Dowex 50-WX2 ion exchange column. After washing the column with 0.1M HCl, the Pt$^{IV}$ complex was removed with 6M HCl and taken down to dryness. It was recrystallised from 1M HCl followed by the addition of acetone. Yield: ~60%.

Analysis: Calcd for PtC$_{20}$H$_{30}$N$_8$Cl$_4$: Pt, 31.30; C.23.12; H, 4.88; N, 17.98; Cl, 22.75. Found: Pt, 29.34; C, 22.17; H, 5.07; N, 18.88; Cl, 22.85

The structure was supported by $^1$H NMR spectrum.

EXAMPLE 7

Preparation of [Rh(sepulchrate)](ClO$_4$)$_3$

To a stirred solution of Li$_2$CO$_3$ (2.0 g) in a solution of [Rh(en)$_3$]Cl$_3$ (0.88 g, 2×10$^{-3}$ mol) in H$_2$O (10 ml) was added aqueous ammonia (2.43 ml, 3.6×10$^{-2}$ mol) diluted to 17.5 ml and aqueous formaldehyde (17.5 ml, 2.1×10$^{-1}$ mol). The solutions were added separately and dropwise over 2.5 h using a peristaltic pump. The pH of the reaction mixture was then adjusted to ~4 with glacial acetic acid and sorbed on an ion exchange column (Dowex 50-WX2,H$^+$ form, 2×10 cm). The column was washed with 0.1M HCl and the complexes removed from the column with 3M HCl. The eluate was taken down to dryness on a vacuum evaporator. The isolated compound was dissolved in H$_2$O and precipitated with LiClO$_4$. The perchlorate salt was recrystallised twice from water and LiClO$_4$. Yield ~50%.

Analysis: Calcd for RhC$_{12}$H$_{30}$N$_8$Cl$_3$O$_{12}$: C, 20.96; H, 4.40; N, 16.30; Cl, 15.47. Found: C, 21.10; H, 4.86; N, 15.36; Cl, 15.31.

The structure was supported by $^1$H NMR spectrum

EXAMPLE 8

Introduction of other functional groups (a) When [Co(diamsar)]$^{3+}$ was treated with NO$^+$ in the presence of Cl$^-$, compounds of the general formula:

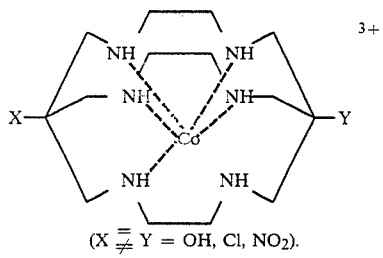

$(X \not= Y = OH, Cl, NO_2)$.

were produced.

(b) [Co(dichlosar)]$^{3+}$ (X=Y=Cl) upon treatment with Zn dust and HCl gave

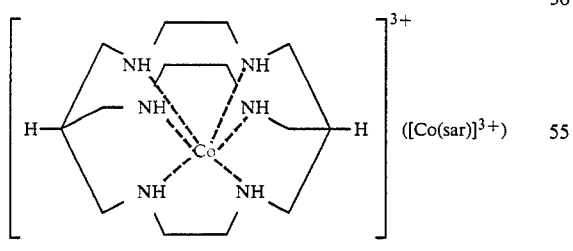

The rate constant (R$_{ox}$) for the reduction of oxygen and oxidation of [Co(sar)]$^{2+}$ under the same conditions as described in Example 3 is found to be 70M$^{-1}$S$^{-1}$.

EXAMPLE 9

In alternative synthesis of the novel complexes of this invention, complexes of the "sen" ligand of the formula:

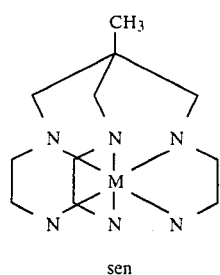

sen (R. W. Green, K. W. Catchpole, A. T. Phillips, and F. Lions, *Inorg. Chem.*, 1963, 2, 597) can be capped with the NH$_3$ and CH$_2$O reagents to form "azamesar" complexes of the formula:

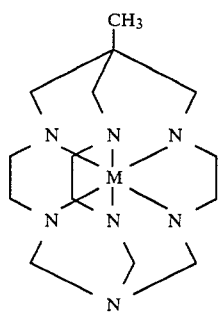

The use of other nucleophiles such as nitromethane or tetra(methylene hydroxy) phosphinium chloride, leads respectively to the "nomesar" complex of the formula:

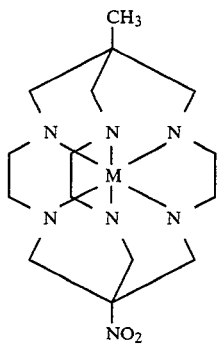

or the complex of the formula:

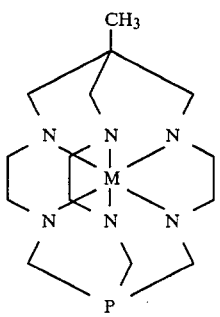

Reduction of the nitro group to the amine (ammesar) occurs with Zn dust and nitrosation of the amine in aqueous solution leads to the hydroxy and chloro (chlormesar) derivatives (in the presence of Cl⁻). Reductive elimination has also been effected to replace Cl by H to give the parent (mesar) ion, as follows:

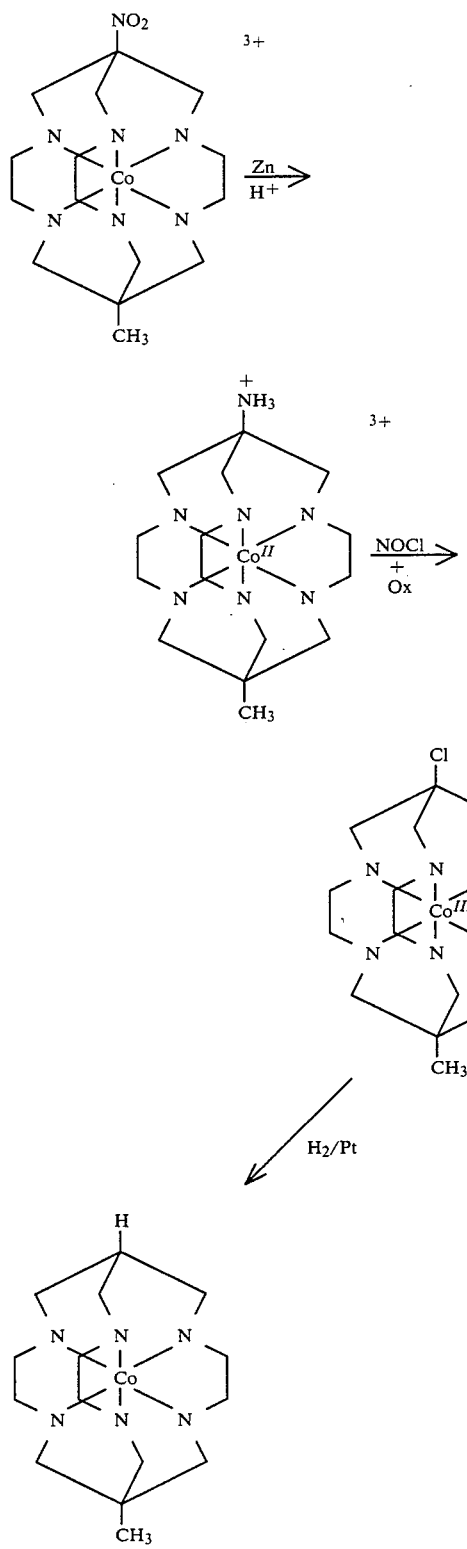

The details given above within the general concept of the production of $H_2O_2$ in accordance with this invention are not to be regarded as limiting and alternative procedures for putting the invention into effect are also within the said concept, for example an electrochemical reduction of the complex when supported on an ion exchange resin, instead of zinc dust, may be used with certain complexes or under certain conditions, or a liquid phase in which reduction or oxidation might be carried out may be varied in composition. All of these modifications are within the general concept of the present invention.

We claim:

1. A metal ion coordination complex of the formula:

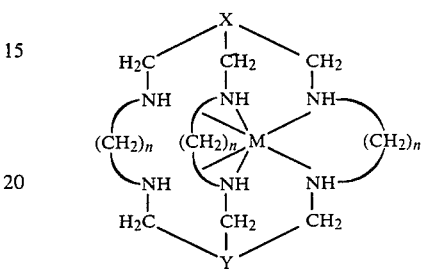

in which n represents 2; M represents a metal ion having at least two oxidation states in which it forms stable coordination complexes selected from the group consisting of ions of Co, Rh, Pt, Cr, Cu, Re, Mo, W, Ni, V and Fe; X represents ≡C—CH₃; and Y represents ≡N or ≡C—R''' wherein R''' represents hydrogen, halogen, nitro, nitroso, amino, hydroxy or alkyl having 1 to 6 carbon atoms.

2. A metal ion coordination complex having the formula:

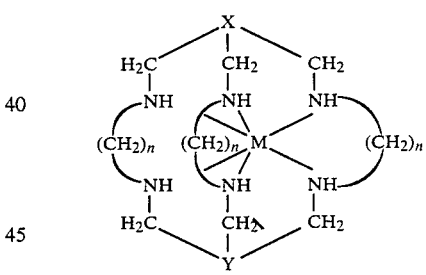

in which n represents 2; M represents a cobalt ion; X and Y each represent ≡C—NO₂, ≡C—NH₂, ≡C—Cl or ≡C—H, or X represents ≡C—CH₃ and Y represent ≡C—H.

3. A metal ion coordination complex of the formula:

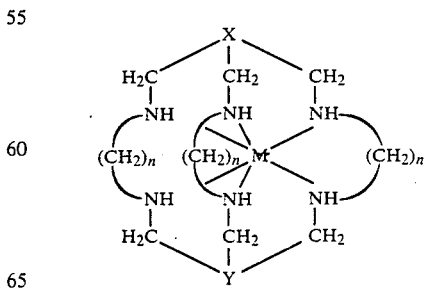

in which n represents 2; M is Pt, and X and Y each represent ≡C—NO₂.

4. A process for the preparation of a complex according to claim 1 wherein X represents ≡C—CH₃, which comprises the steps of reacting a metal chelate of 1,9-diamino-5-(methyl)-5-(4-amino-2-azabutyl)-3,7-diazanonane of the formula:
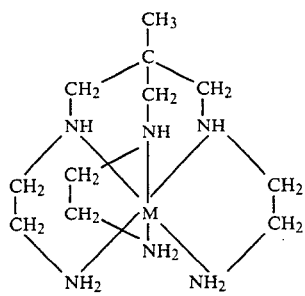
in which M is as defined in claim 1, with formaldehyde and a nucleophile capable of yielding a capping group of the formula ≡N or ≡C—R⁴, wherein R⁴ is NO₂.
* * * * *